(12) United States Patent
Hirose et al.

(10) Patent No.: US 8,902,417 B2
(45) Date of Patent: Dec. 2, 2014

(54) INSPECTION APPARATUS

(75) Inventors: Nobuaki Hirose, Hitachinaka (JP);
Takahiro Jingu, Takasaki (JP);
Hidetoshi Nishiyama, Hitachinaka (JP);
Kazuo Takahashi, Naka-gun (JP);
Hisashi Hatano, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 13/993,814

(22) PCT Filed: Nov. 9, 2011

(86) PCT No.: PCT/JP2011/006246
§ 371 (c)(1),
(2), (4) Date: Jun. 27, 2013

(87) PCT Pub. No.: WO2012/090373
PCT Pub. Date: Jul. 5, 2012

(65) Prior Publication Data
US 2013/0271754 A1 Oct. 17, 2013

(30) Foreign Application Priority Data
Dec. 27, 2010 (JP) .................................. 2010-289101

(51) Int. Cl.
*G01N 21/00* (2006.01)
*G01N 21/956* (2006.01)
*G01N 21/95* (2006.01)

(52) U.S. Cl.
CPC ...... *G01N 21/9501* (2013.01); *G01N 21/95623* (2013.01)
USPC .................................. 356/237.2; 356/237.4

(58) Field of Classification Search
USPC ............................................ 356/237.1–237.5
See application file for complete search history.

(56) References Cited

U.S. PATENT DOCUMENTS

| | | | | |
|---|---|---|---|---|
| 4,922,308 A | * | 5/1990 | Noguchi et al. | ............ 356/237.4 |
| 6,545,755 B1 | * | 4/2003 | Ishihama et al. | .............. 356/301 |
| 2007/0229809 A1 | | 10/2007 | Belyaev et al. | |
| 2008/0068593 A1 | | 3/2008 | Nakano et al. | |
| 2008/0094616 A1 | * | 4/2008 | Tanaka | ........................ 356/237.2 |
| 2008/0204736 A1 | | 8/2008 | Chikamatsu et al. | |

FOREIGN PATENT DOCUMENTS

| | | |
|---|---|---|
| JP | 06-082380 A | 3/1994 |
| JP | 07-113760 A | 5/1995 |
| JP | 11-352075 A | 12/1999 |
| JP | 2004-093252 A | 3/2004 |
| JP | 2005-345221 A | 12/2005 |
| JP | 2007-279040 A | 10/2007 |

(Continued)

*Primary Examiner* — Michael P Stafira
(74) *Attorney, Agent, or Firm* — Mattingly & Malur, PC

(57) ABSTRACT

This invention implements reduction in the amount of background-scattered light from a semiconductor wafer surface and highly sensitive inspection, without increasing the number of detectors. A surface inspection apparatus that detects defects on the surface of an object (semiconductor wafer surface) to be inspected, by irradiating the surface of the object with a beam of light such as laser light and detecting the light reflected or scattered from the surface; wherein a widely apertured lens with an optical Fourier transform function is disposed between the object to be inspected and a detector, a filter variable in position as well in aperture diameter is provided on a Fourier transform plane, and background-scattered light from the semiconductor wafer surface is effectively blocked, whereby only a signal from a defect such as a foreign substance is detected.

16 Claims, 6 Drawing Sheets

(56) References Cited

FOREIGN PATENT DOCUMENTS

| | | |
|---|---|---|
| JP | 2008-096430 A | 4/2008 |
| JP | 2008-116405 A | 5/2008 |
| JP | 2008-241570 A | 10/2008 |
| JP | 2008-241688 A | 10/2008 |
| JP | 2010-190722 A | 9/2010 |
| JP | 2010-256148 A | 11/2010 |

* cited by examiner

INSPECTION APPARATUS

TECHNICAL FIELD

The present invention relates to an apparatus and method for inspecting defects present on substrates. For example, the invention is directed to an apparatus and method for inspecting defects on a surface of a semiconductor wafer.

BACKGROUND ART

If defects such as foreign substances or flaws are present on a mirror-like surface of a wafer used in semiconductor-manufacturing processes, the defects affect a production yield of the semiconductor devices. It is therefore vital to inspect the defects on the mirror-like wafer surface. Additionally, management standards relating to the defects are required to be raised to higher levels with the progress of the semiconductor device manufacturing processes. Surface inspection apparatuses are used for such defect management. Known surface inspection apparatuses detect defects on the surface of an object to be inspected, by irradiating the surface of the object with a beam of light such as laser light and detecting the light reflected or scattered from the surface.

Examples of surface inspection apparatuses are described below. The surface inspection apparatus described in Patent Document 1 listed below includes a plurality of detectors each different in elevation angle in addition to azimuthal angle, and is constructed so that the selection of a detector receiving the strong light scattered from foreign substances and/or defects enables background-scattered light to be suppressed for enhanced detection sensitivity for foreign substances and defects.

Although not intended for wafers with a mirror-like surface, surface inspection apparatuses for wafers with circuit patterns formed thereupon include one described in Patent Document 2 listed below. Surface inspection apparatuses for other semiconductor substrates include ones described in Patent Documents 3 to 8 listed below.

PRIOR ART LITERATURE

Patent Documents

Patent Document 1: JP-2008-241570-A
Patent Document 2: JP-2004-93252-A
Patent Document 3: JP-1995-113760-A
Patent Document 4: JP-2008-116405-A
Patent Document 5: JP-1999-352075-A
Patent Document 6: JP-2010-190722-A
Patent Document 7: JP-2010-256148-A
Patent Document 8: JP-1994-082380-A

SUMMARY OF THE INVENTION

Problems to be Solved by the Invention

The foregoing surface inspection apparatuses are required to detect microscopic defects, which is to say, to have high sensitivity. In this context, to achieve high sensitivity, it has been considered to be effective in the present invention to reduce impacts of background-scattered light. In addition, it has been found in the present invention that a spatial distribution of the background-scattered light from a semiconductor wafer surface differs according to particular intervals of surface roughness, for example.

Here, in the apparatus configuration according to Patent Document 1, the degree of freedom of a scattered-light detection range (elevation and azimuthal angles) is limited by the number of detectors. To attain even higher sensitivity in the future, therefore, there is a need to increase the number of detectors and that of signal processing operations to be performed according to the number of detectors, and thus, these increases make it unavoidable to upscale the hardware and to increase the materials costs required.

Patent Document 2 discloses a spatial filter, and this filter is used only to block the light diffracted from the circuit patterns. No information is disclosed as to background-scattered light and association between it and a spatial distribution.

Patent Documents 3 to 8 disclose no information on a spatial distribution of background-scattered light, either.

The present invention has been made with the above problems in mind, and an object of the invention is to implement highly sensitive inspection.

Means for Solving the Problems

In order to attain the above object, a surface inspection apparatus according to an aspect of the present invention irradiates a surface of an object to be inspected, with a beam of light, and depending on detection intensity of the light reflected or scattered, inspects whether defects are present on the surface of the object; wherein a widely apertured lens with an optical Fourier transform function is disposed between the object to be inspected and a detector, and a filter variable in position as well in aperture diameter is provided on a Fourier transform plane.

In other terms, the above can be expressed as follows. That is to say, on the Fourier plane, information on the light scattered from a wafer is expressed in optical Fourier transform fashion by use of diffraction, the expression form of which indicates that information on intensity and phase of the light is obtained on the Fourier plane. On the Fourier plane, information on scattered light from a defect is obtained separately from that of background-scattered light. In other words, it is one aspect of the present invention that on the Fourier plane, if the scattered light from the defect is passed through and the background-scattered light is blocked, only the scattered light from the defect can be detected and high sensitivity obtained. It is another aspect of the present invention that instead of the number of light-collecting optical systems being increased as in Patent Document 1, if any signal is extracted on the Fourier plane after the light has been collected, this provides advantageous effects equivalent to or greater than those obtained by increasing detectors in Patent Document 1.

In this apparatus configuration, the background-scattered light from the surface of the semiconductor wafer can be blocked effectively by optimizing the aperture diameter and position of the filter provided on the Fourier plane.

Effects of the Invention

In accordance with the present invention having the above configuration, even when the background-scattered light from the surface of the semiconductor wafer differs in distribution, high sensitivity can be attained since the background-scattered light can be blocked effectively by changing the position as well as aperture diameter of the filter provided on the Fourier plane.

MODE FOR CARRYING OUT THE INVENTION

Hereunder, embodiments of the present invention will be described referring to the accompanying drawings.

First Embodiment

Figure 1:
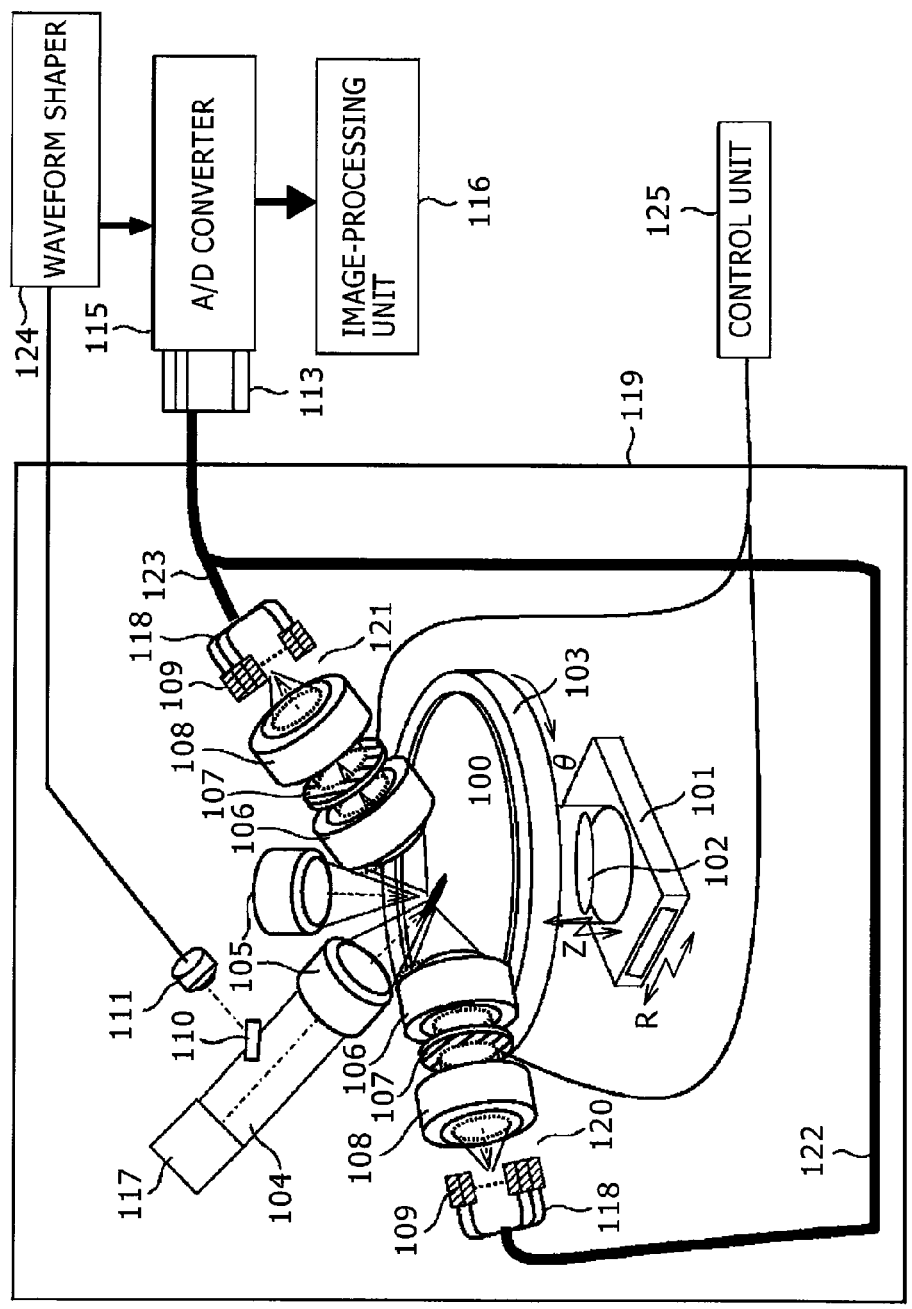
FIG. 1 is a diagram showing a schematic configuration of a surface inspection apparatus according to a first embodiment.

FIG. 1 is a diagram showing a configuration of a surface inspection apparatus according to a first embodiment. First, a transport system that moves a wafer 100 is described here. The wafer 100 is immobilized by a θ-stage 103. The wafer 100 has its height controlled by a Z-stage 102 (auto-focusing). Additionally, the wafer 100 is moved rectilinearly in one direction by an R-stage 101. The wafer 100 is rotated at high speed by the θ-stage 103 and further moved rectilinearly in a radial direction by the R-stage 101. Thus the wafer has its entire surface scanned in relative fashion with respect to light described later herein.

Next, an optical system for illuminating the wafer 100 with light is described here. Light from a pulse light source 117 is delivered through a lens 105. In the first embodiment, the lens 105 is, for example, a cylindrical lens, through which the wafer 100 is illuminated with a slit form of light obliquely. That is to say, a darkfield image is detected in the present embodiment.

Next, an optical system that detects the light scattered from the wafer 100 is described here. The optical system for detection includes a first imaging optical system 120, a second imaging optical system 121, an optical fiber 118, and a sensor 113 having a plurality of pixels. The elements of the detection optical system are each arranged at a different elevation angle in addition to a different azimuthal angle, with respect to the wafer 100 (the elevation and azimuthal angles can be freely combined).

The first and second imaging optical systems are described below. The first and second imaging optical systems 120 and 121 both include a Fourier lens 106 that detects the light scattered from the wafer 100, a background-scattered light removing element 107 disposed at rear of the Fourier lens 106, and an imaging lens 108 disposed at further rear of the background-scattered light removing element 107. Both optical systems 120 and 121 also include a microlens array 109 that collects the darkfield image that the imaging lens 108 has formed, into an optical fiber 118 described later herein.

The Fourier lens 106 is a high-NA lens. It is an elliptically shaped lens whose NA is, for example, greater in an azimuthal angle direction than in an elevation angle direction, with respect to the wafer 100. For example, the NA of this lens is 0.35 in the elevation angle direction and 0.8 in the azimuthal angle direction (nearly 150° in azimuthal angle). This allows a wide range of scattered light to be accepted with one lens. In addition, stacking of imaging optical systems in the elevation angle direction can also be conducted.

Furthermore, the image that has been formed by the imaging lens 108 is first collected by the microlens array 109 disposed at a focal point of the imaging lens 108, and then guided into the optical fiber 118 disposed at rear of the microlens array 109. The light, while maintaining the image intact, is further guided into the multi-pixel sensor 113 disposed outside an enclosure 119 of the apparatus, by the optical fiber 118, and thus detected as another darkfield image by the sensor 113.

A first section 122 in an optical fiber 112, for guiding a first darkfield image from the first imaging optical system 120, and a second section 123 for guiding a second darkfield image from the second imaging optical system 121 differ from each other in optical path length, and thus the first darkfield image and the second darkfield image are detected in different timing by the sensor 113. This allows the darkfield images to be detected with one sensor. An independent sensor may, of course, be provided for each optical fiber. The sensor 113 here is, for example, a multi-pixel photon counter (MPPC).

Image processing is next described. Each detected darkfield image is converted from analog signal form into digital signal form by an A/D converter 115. By this time, a waveform of the illumination light 104 from the pulse light source 117 is already measured as light-emission timing by a photodiode 111. Since the signal detected by the A/D converter 115 is delayed, a delay signal corresponding to a delay time of the A/D converter 115 is also already added by a waveform shaper 124 to the light-emission timing that the photodiode 111 measured. On the basis of the timing signal having the delay signal added thereto, the A/D converter 115 acquires the darkfield image. This allows so-called gated sampling. The acquired darkfield image is compared with a threshold value by an image-processing unit 116. If the signal level is greater than the threshold value, the signal is recognized as a signal due to a defect.

Next, the background-scattered light removing element 107 is described in detail below using FIGS. 2 to 7. The background-scattered light removing element 107 includes a spatial filter 201 (described later herein) that is used to remove the light that is background-scattered from the wafer 100, and an attenuator 701 disposed at rear of the spatial filter 201 in order to control the amount of light detected.

Figure 2:
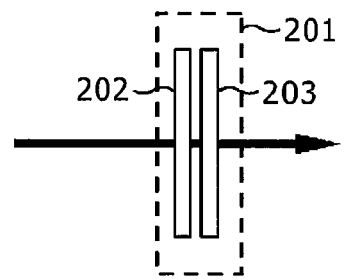
FIG. 2 is a diagram showing an exemplary configuration of a spatial filter in the first embodiment.

FIG. 2 is a diagram showing an exemplary configuration of the spatial filter. The spatial filter 201 includes a first light-blocking plate 202 and a second light-blocking plate 203. The first light-blocking plate 202 and the second light-blocking plate 203 each have an aperture. The aperture can have an aperture diameter optionally changeable, as of a stop. Hereinafter, the aperture in the first light-blocking plate 202 is referred to as the first aperture 204, and the aperture in the second light-blocking plate 203, as the second aperture 205.

In the present embodiment, the first aperture 204 and the second aperture 205 are overlapped, one upon the other, to create any light-blocking pattern.

Figure 3:
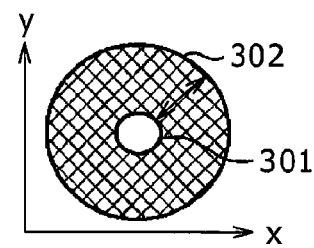
FIG. 3 is a diagram showing an exemplary shape of the spatial filter in the first embodiment.

FIG. 3 is a diagram showing the first light-blocking Plate 202 and the second light-blocking plate 203. Each of the first aperture 204 and the second aperture 205 can optionally change a dimensional ratio of an aperture 301 and a first light-blocking portion 302, as shown in FIG. 3. Additionally, the first light-blocking plate 202 and the second light-blocking plate 203 can freely move in a plane parallel to the Fourier plane, for example in a moving mechanism of a motor or ball screw.

Next, a method of using the first aperture 204 and the second aperture 205 is described below. On the Fourier plane posterior to the lens aperture, the present embodiment freely changes a position as well as shape of a portion which removes background-scattered light, and a position as well as shape of a portion which lets scattered light pass through, the scattered light in the latter portion being inclusive of the scattered light denoting a defect.

Figure 4:
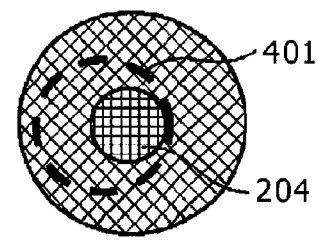
FIG. 4 is a diagram showing a first variation in the first embodiment.

FIG. 4 shows a first variation, an example of using one filter with the first light-blocking plate 202 (this may be replaced by the second light-blocking plate 203). Referring to FIG. 4, the first aperture 204 is formed at a position shifted from a central axis, inside an aperture 401 of the Fourier lens 106, as shown. In addition, the aperture 401 in the Fourier lens 106 is present inside the first light-blocking portion 302. The scattered light from the wafer 100 passes only through a region at which the aperture 401 in the Fourier lens 106 and the first aperture 204 overlap.

Next, a second variation is described below using FIG. 5. The second variation, which is another example of using one filter with the first light-blocking plate 202 (this may be replaced by the second light-blocking plate 203), differs from the first variation in that the aperture 401 in the Fourier lens 106 and the first aperture 204 partly overlap.

Figure 6:
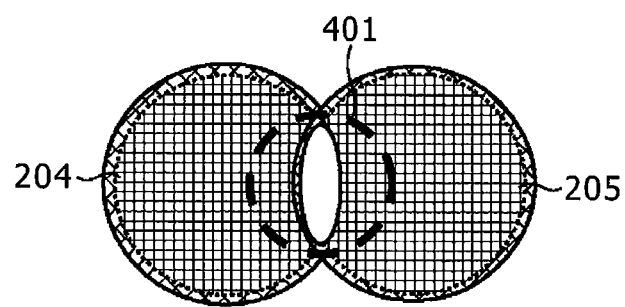
FIG. 6 is a diagram showing a third variation in the first embodiment.

Next, a third variation is described below using FIG. 6. The third variation is an example of using the first light-blocking plate 202 and the second light-blocking plate 203. Referring to FIG. 6, the first aperture 204 and the second aperture 205 partly overlap, the overlapping region 601 lying inside the aperture 401 of the Fourier lens. The scattered light from the wafer 100 passes only through the region 601.

Figure 5:
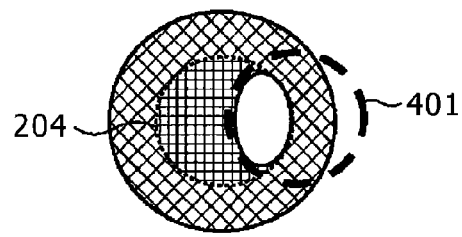
FIG. 5 is a diagram showing a second variation in the first embodiment.

As described in FIGS. 4 to 6, since a control unit 125 controls respective sizes, positions, and overlapping forms of the apertures, and relative positions of these apertures with respect to the aperture in the Fourier lens, any background-scattered light components existing at specific positions on the Fourier plane can be removed effectively, even if a spatial distribution of the background-scattered light from the wafer 100 differs according to particular intervals of surface roughness.

Accordingly, it is another beneficial effect that undesired light (e.g., diffracted light) that the light detected may include can be rendered less influential by providing the above apertures with an uneven structure, more specifically a zigzag structure. If an optical nature of the undesired light is known in advance, the provided structures can also be associated with the optical nature of the undesired light. In this case, the impacts of the diffracted light can be reduced more effectively.

Furthermore, if appropriate light-blocking parameters corresponding to several specific kinds of defects are stored in a memory, only defects of any one of the stored kinds can be detected with high sensitivity by conducting control with the control unit 125 so that a light-blocking parameter corresponding to a known surface state or the specific kind of defect is selected prior to inspection. The light-blocking parameters here refer to, for example, surface roughness, a distribution state of any background-scattered light components corresponding to surface roughness, the sizes, positions, and overlapping forms of the apertures, and the relative positions of these apertures with respect to the aperture in the Fourier lens. In addition, the several specific kinds of defects refer to flaws, foreign substances, crystal defects, and the like.

Figure 7:
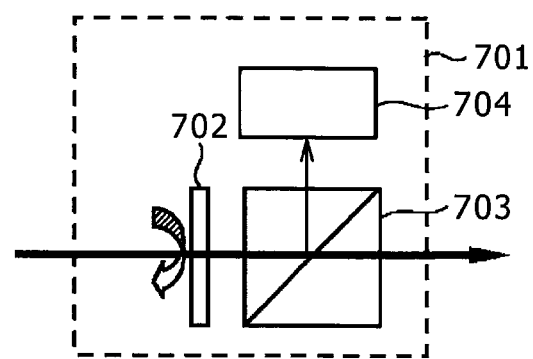
FIG. 7 is a diagram showing an exemplary configuration of an attenuator in the first embodiment.

Next, the attenuator 701 is described below using FIG. 7. The attenuator 701, disposed at the rear of the spatial filter 201, includes a half-wave plate 702, a polarizing beam splitter 703 disposed at rear of the half-wave plate 702, and a damper 704 disposed at a reflecting side of the polarizing beam splitter 703 in order to attenuate and absorb scattered light. Light that has passed the polarizing beam splitter 703 further passes the imaging lens 108 and the like, thus being detected as a darkfield image by the sensor 113.

At this time, the A/D converter 115 measures brightness of the darkfield image in the sensor 113, and if the brightness of a region of the darkfield image is in excess of a threshold value, the converter 115 determines a saturation region to exist in the darkfield image. The half-wave plate 702 rotates according to a particular result of the determination. Thus the saturation of the brightness of the darkfield image can be suppressed.

In the present embodiment, the first and second imaging optical systems 120 and 121 each include the attenuator. This allows effective detection of defects, even if strong light is scattered in a certain direction.

Besides, if appropriate light-blocking parameters corresponding to several specific kinds of defects are stored in a memory, only defects of any one of the stored kinds can be detected with high sensitivity, as well as with suppressed saturation of the darkfield image, by controlling the attenuator while conducting control so that a light-blocking parameter corresponding to a known surface state or the specific kind of defect is selected prior to inspection. The light-blocking parameters here refer to, for example, the sizes, positions, and overlapping forms of the apertures, and the relative positions of these apertures with respect to the aperture in the Fourier lens. In addition, the several specific kinds of defects refer to flaws, foreign substances, crystal defects, and the like.

As described above, the present embodiment uses a high-NA lens to collect scattered light and uses a background-scattered light removing element to effectively remove background-scattered light. Thus, highly sensitive detection of defects and more accurate classification of the defects can be achieved with a smaller number of detectors than in conventional techniques.

Second Embodiment

Figure 8:
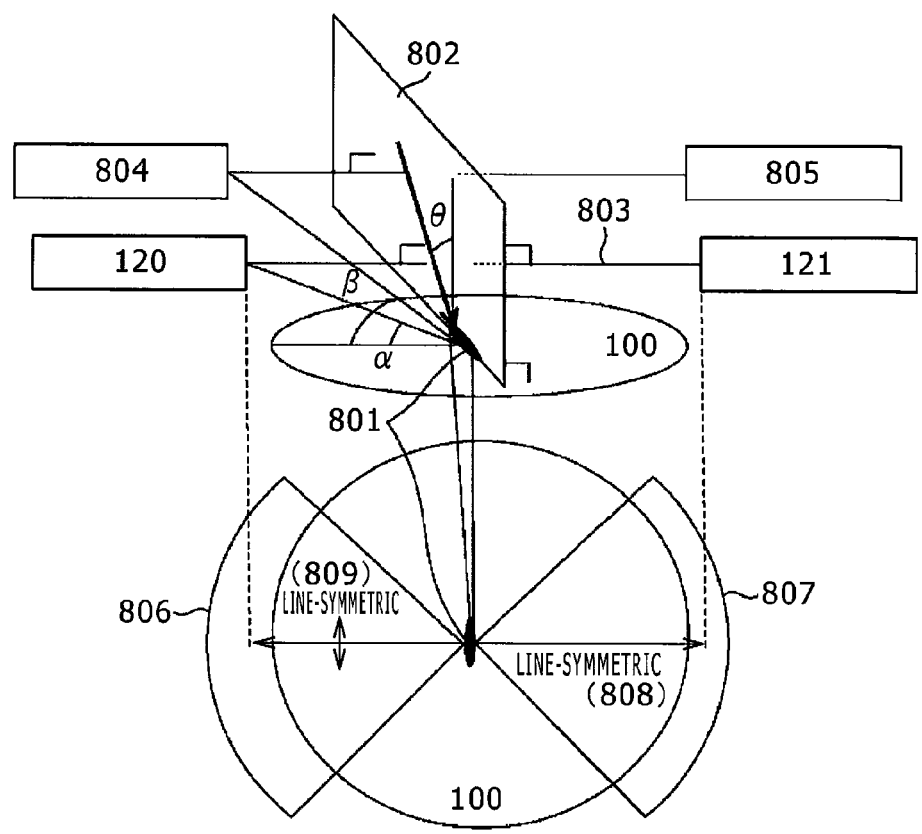
FIG. 8 is a diagram illustrating a second embodiment.

Next, a second embodiment is described below using FIG. 8. In the present embodiment, a wafer 100 is illuminated with linear illumination light 801 from an oblique direction (i.e., at an angle of incidence, θ). Unlike the first and second imaging optical systems 120 and 121 described in the first embodiment, first and second imaging optical systems 120 and 121 in the second embodiment are arranged at an angle of elevation, α, to face each other in a direction 803 perpendicular to a plane of incidence, 802, formed by a line perpendicular to an optical axis of the illumination light 801 and the wafer 100.

Here, when the wafer 100 is viewed from above, a detection aperture 806 in the first imaging optical system 120 and a detection aperture 807 in the second imaging optical system 121 are line-symmetrical (808) with respect to a longitudinal direction of the illumination light 801 and line-symmetrical (809) with respect to a line perpendicular to the longitudinal direction of the illumination light 801. This arrangement of the first and second imaging optical systems 120 and 121 allows highly sensitive detection of defects.

Additionally providing a third imaging optical system 804 and a fourth imaging optical system 805 at an angle of elevation, β, that is higher than that of the first and second imaging optical systems 120 and 121, allows even more highly sensitive detection of defects.

Depending on their properties such as shape, defects vary in a scattering pattern of scattered light. Arranging the third and fourth imaging optical system 804 and 805 with attention attached to this characteristic and setting appropriate aperture patterns that correspond to the scattering patterns of specific defects will likewise allow only the specific defects to be detected with high sensitivity.

Third Embodiment

Figure 9:
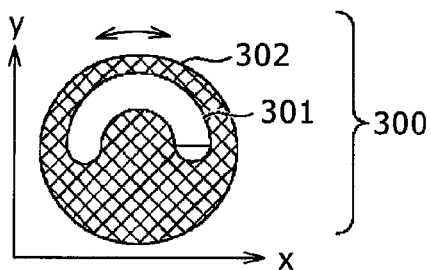
FIG. 9 is a first diagram illustrating a third embodiment.
Figure 10:
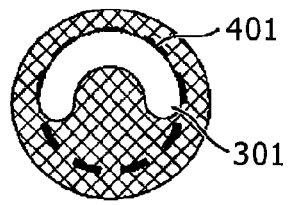
FIG. 10 is a second diagram illustrating the third embodiment.

Next, a third embodiment is described below using FIGS. 9 to 12. Elements different from those of the first and second embodiments are mainly described in the third embodiment. FIG. 9 illustrates a spatial filter used in the third embodiment. The spatial filter 300 in the present embodiment includes a light-blocking plate 302 and an arc-shaped aperture 301 formed on the light-blocking plate 302. In addition, the spatial filter 300 can freely move by means of a mechanism that moves in parallel with respect to a Fourier plane, and a mechanism that rotates about the Fourier plane. The spatial filter 300 is effective for defect-scattered light whose angle of elevation is known. Moving the aperture 301 into an aperture 401 of a Fourier lens, as shown in FIG. 10, makes it effective to detect scattered light having a known elevation and a relatively wide expanse of directivity.

Figure 11:
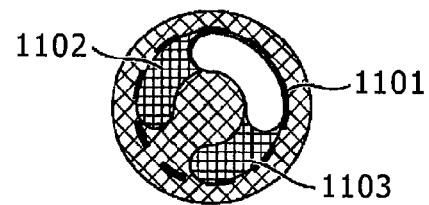
FIG. 11 is a third diagram illustrating the third embodiment.

Furthermore, the spatial filter 300 in the present embodiment can likewise be constructed by combining the light-blocking plate 302 with other light-blocking plates. For example, if as shown in FIG. 11, light-blocking plates 1102 and 1103 of an arc shape are placed across the aperture 301 disposed in the aperture 401 of the Fourier lens, an arc-shaped aperture 1101 shorter than the aperture 301 can be obtained (the light-blocking plates 1102, 1103 may be replaced by the first light-blocking plate 202 and the second light-blocking plate 203, respectively).

Figure 12:
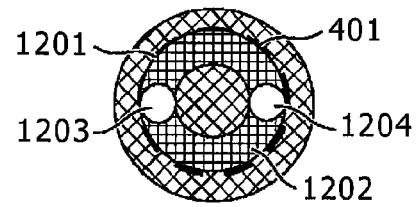
FIG. 12 is a fourth diagram illustrating the third embodiment.

Moreover, substantially point-symmetrical apertures 1203 and 1204 may be formed by, as shown in FIG. 12, rotating two arc-like apertures similar to the arc-shaped aperture 301, through 180 degrees to overlap both and blocking a non-overlapped region with light-blocking plates 1201 and 1202.

Fourth Embodiment

Figure 13:
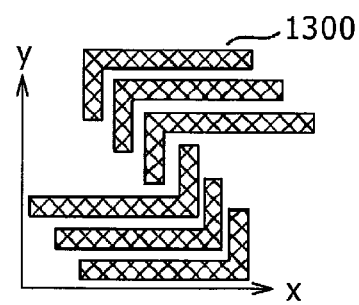
FIG. 13 is a first diagram illustrating a fourth embodiment.
Figure 14:
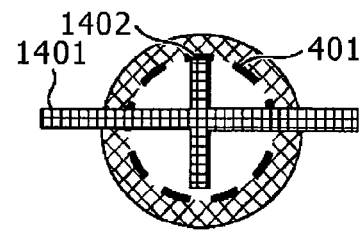
FIG. 14 is a second diagram illustrating the fourth embodiment.

Next, a fourth embodiment is described below using FIGS. 13 to 17. In the present embodiment, a light-blocking pattern with a high degree of freedom is formed using bar-shaped, for example L-shaped, light-blocking plates. FIG. 13 is an explanatory diagram of the present embodiment. In the present embodiment, a spatial filter is formed using the plurality of L-shaped light-blocking plates 1300. The light-blocking plates 1300 each include a mechanism that moves in parallel in a Fourier plane. In the present embodiment, as in a first variation shown in FIG. 14, for example, light-blocking plates 1401 and 1402 are arranged to cross each other in an aperture 401 of a Fourier lens. This arrangement effectively blocks background-scattered light, even if the background-scattered light has high intensity in anterior, posterior, and straightly opposing directions with respect to an illuminating direction.

Figure 15:
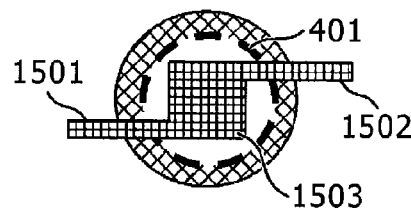
FIG. 15 is a third diagram illustrating the fourth embodiment.

FIG. 15 is a diagram showing a second variation of the fourth embodiment. Shown in FIG. 15 is an example of forming a substantially square light-blocking pattern 1503 by bringing light-blocking plates 1501 and 1502 into mutual contact to substantially block only a nearly central portion of an aperture 401 in a Fourier lens. The second variation is particularly effective for strong background-scattered light occurring in a direction normal to a target wafer.

Figure 16:
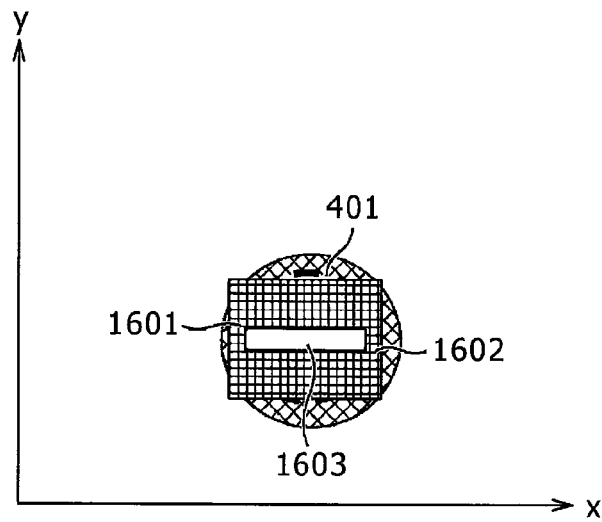
FIG. 16 is a fourth diagram illustrating the fourth embodiment.
Figure 17:
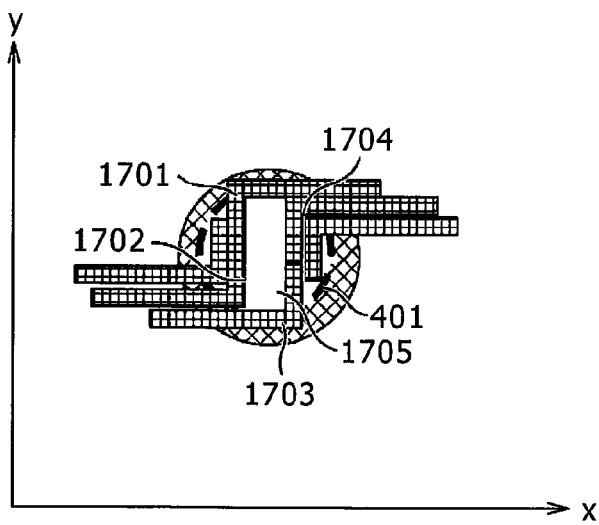
FIG. 17 is a fifth diagram illustrating the fourth embodiment.

Additionally, as in a third variation shown in FIG. 16, light-blocking plates 1501 and 1502 may be arranged to form a substantially rectangular aperture 1603 in a nearly central portion of an aperture 401 in a Fourier lens. In this case, only light having a predetermined spatial frequency in a Y direction can be made to pass through, by forming the aperture on a Fourier plane so that the aperture has a surface wide in an X direction and narrow in the Y direction.

FIG. 16 is a diagram showing a fourth variation. In FIG. 16, contrary to the third variation, an aperture 1705 short in the X direction and long in the Y direction is formed on a Fourier transform plane by use of light-blocking plates 1701 to 1704. Thus an aperture surface narrow in the X direction and wide in the Y direction is created, whereby only light having a predetermined spatial frequency in the X direction can be made to pass.

Furthermore, using the third or fourth variation allows frequency analysis of the background-scattered light and hence, determination of an efficient light-blocking pattern even for a wafer unknown in distribution state of the background-scattered light.

DESCRIPTION OF REFERENCE NUMERALS

100 Wafer
101 R-stage
102 Z-stage
103 θ-stage
104 Illumination light
105 Lens
106 Fourier lens
107 Background-scattered light removing element
108 Imaging lens
109 Microlens array
110 Mirror
111 Photodiode
112, 118 Optical fibers
113 Sensor
115 A/D converter
116 Image-processing unit
117 Pulse light source
119 Apparatus enclosure
120 First optical system for imaging
121 Second optical system for imaging
122 First section
123 Second section
124 Waveform shaper
125 Filter control unit
201 Spatial filter
202 First light-blocking plate
203 Second light-blocking plate
204 First aperture
205 Second aperture
301 Aperture in filter
302 First light-blocking portion
401 Aperture in Fourier lens 701 Attenuator
702 Half-wave plate
703 Polarizing beam splitter
704 Damper

The invention claimed is:

1. An inspection apparatus for inspecting a defect present on a substrate, the apparatus comprising:
   a mounting unit on which the substrate is to be mounted;
   an irradiating unit that irradiates the substrate with light;
   a detection unit that collects the light from the substrate and forms an image; and
   a processing unit that detects the defect from a detection result produced by the detection unit,
   wherein the detection unit includes:
      a detector that detects the formed image;
      a background-scattered light removing element configured to remove the light that is background-scattered from the substrate; and
      a lens with an optical Fourier transform function disposed between the substrate and the background-scattered light removing element,
   wherein the background-scattered light removing element removes the background-scattered light according to a type of the defect to be detected and a surface state of the substrate, and
   the background-scattered light removing element is disposed on a Fourier transform plane formed by the lens.

2. The inspection apparatus according to claim 1, wherein the detection unit further includes a high-NA lens disposed anteriorly to the background-scattered light removing element.

3. The inspection apparatus according to claim 2, wherein the lens is an elliptically shaped lens whose NA is greater in an azimuthal angle direction than in an elevation angle direction, with respect to the substrate.

4. The inspection apparatus according to claim 1, wherein the background-scattered light removing element includes a first light-blocking plate fitted with a first aperture, the first aperture having a variable diameter.

5. The inspection apparatus according to claim 4, further comprising
   a first moving unit that changes a position of the first light-blocking plate.

6. The inspection apparatus according to claim 4, wherein the background-scattered light removing element includes a second light-blocking plate fitted with a second aperture, the second aperture having a variable diameter.

7. The inspection apparatus according to claim 6, further comprising
   a second moving unit that changes a position of the second light-blocking plate.

8. The inspection apparatus according to claim 1, further comprising
   an optical fiber array, disposed between the background-scattered light removing element and the detector, for propagating the image to the detector.

9. The inspection apparatus according to claim 1, further comprising
   a memory unit configured to store one or more light blocking parameters corresponding to several types of defects; and
   a control unit configured to select an appropriate light blocking parameter based on a known surface state of the substrate or a specific type of defect.

10. The inspection apparatus according to claim 9, wherein the control unit further controls an attenuator to suppress saturation of the image.

11. The inspection apparatus according to claim 1, wherein the background-scattered light removing element is an aperture, and the position and the shape of the aperture is variable.

12. The inspection apparatus according to claim 11, wherein
   the aperture is formed by plural members to remove background-scattered light, and the position of the members are adjustable.

13. The inspection apparatus according to claim 11, wherein
   the background-scattered light removing element is a light-blocking plate with an arc-shaped aperture.

14. The inspection apparatus according to claim 11, wherein
   the background-scattered light removing element is a light-blocking plate with substantially point-symmetrical apertures.

15. The inspection apparatus according to claim 11, wherein
   the background-scattered light removing element is a light-blocking plate with apertures formed by L-shaped light-blocking plates arranged to cross each other.

16. The inspection apparatus according to claim 11, wherein
   the background-scattered light removing element is substantially square light-blocking pattern.

* * * * *